United States Patent [19]
Bowman et al.

[11] Patent Number: 5,342,673
[45] Date of Patent: Aug. 30, 1994

[54] STERILIZABLE PACKAGING MATERIAL

[75] Inventors: Jane Bowman, Handover, Mass.; Ed Daniel, Landenberg, Pa.; Bob Henn, Wilmington, Del.; Jennifer Levy, Newark, Del.; Neville Vakharia, New Castle, Del.

[73] Assignee: W. L. Gore & Associates, Inc., Newark, Del.

[21] Appl. No.: 21,418

[22] Filed: Feb. 23, 1993

[51] Int. Cl.5 .................................. B32B 27/14
[52] U.S. Cl. .................................. 428/198; 206/438; 206/557; 428/195; 428/284; 428/287; 428/296; 428/304.4; 428/343; 428/354; 428/355; 428/421; 428/422
[58] Field of Search ............... 428/284, 287, 296, 421, 428/422, 195, 198, 304.4, 343, 354, 355; 206/557, 438

[56] References Cited

U.S. PATENT DOCUMENTS

| | | | |
|---|---|---|---|
| 3,123,210 | 3/1964 | Hermanson et al. | 206/63.2 |
| 3,135,455 | 6/1964 | Santangelo | 229/30 |
| 4,270,658 | 6/1981 | Schuster | 206/439 |
| 4,381,848 | 5/1983 | Kahn | 229/43 |
| 4,550,546 | 11/1985 | Raley et al. | 53/425 |
| 4,714,595 | 12/1987 | Anthony et al. | 412/297 |

OTHER PUBLICATIONS

Advance Tech-Data Sheet from Goodyear Tire and Rubber Co., Jun. 1987.
Vitel Speciality Copolyester Resins Data.

*Primary Examiner*—James J. Bell
*Attorney, Agent, or Firm*—Gary A. Samuels

[57] ABSTRACT

A flexible, air permeable, high temperature resistant, bacteria-impermeable packaging material is described. The packaging material is preferably made of nonwoven polyester layers on either side of and bonded to a microporous membrane. One nonwoven is bonded to the membrane with a thermoplastic adhesive.

4 Claims, 6 Drawing Sheets

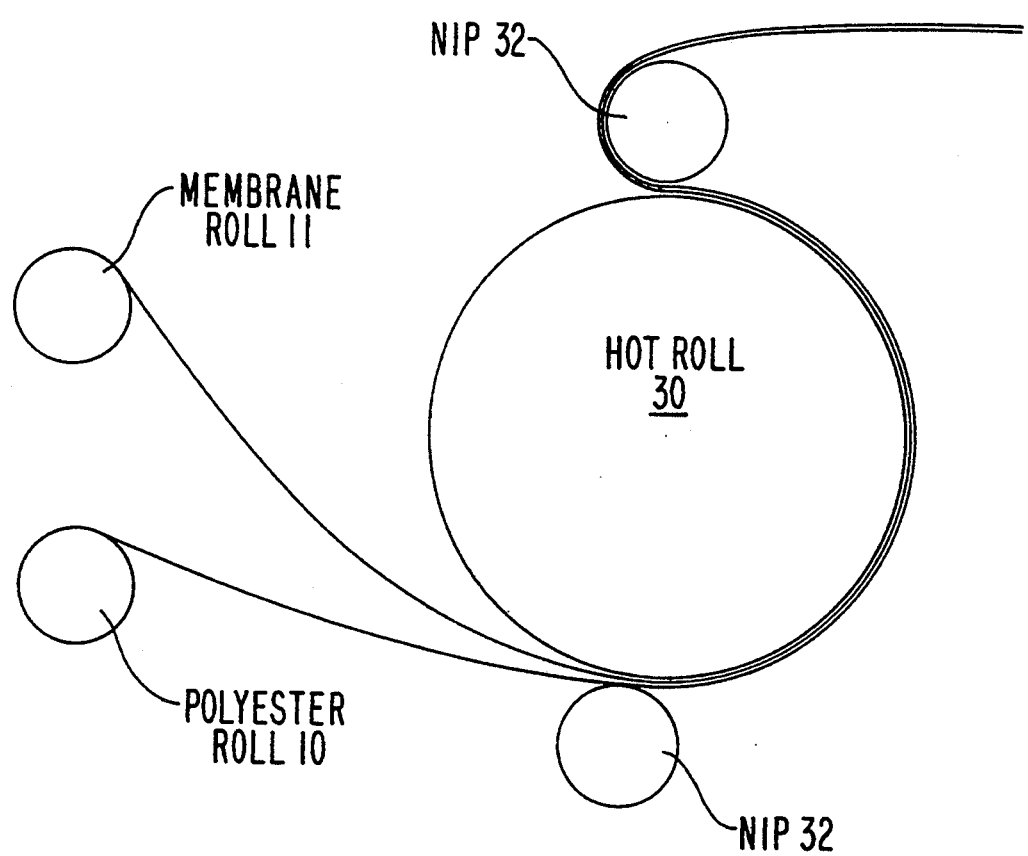

STERILIZABLE PACKAGING MATERIAL

FIELD OF THE INVENTION

This invention relates to a layered sterilizable packaging material made of laminated polymeric films.

BACKGROUND OF THE INVENTION

Sterilizable packaging for medical products is needed to handle, store and transport medical devices, prosthetics, or accessories, such as gauze, needles, scalpels, clamps, sutures and so forth.

Usually, the product is placed in the package, the package sealed, and then the sealed package subjected to sterilizing conditions which sterilize the contents of the package. The seal must be strong enough and durable enough to withstand handling during transportation and storage; but it must be easily opened when the product is needed.

When sterilization is carried out by heating, the packaging or a portion of it must be air and steam-permeable so that the gas, usually air or steam, inside the package can escape as it expands from the heat. On the other hand, the packaging must be constructed in a manner to prevent entry of bacteria and pathogenic organisms after and during sterilization and until the package is subsequently opened.

When the package is a lid/container combination, the lid must be sealable to the container with good integrity of seal, but yet be easily peeled off while preferably leaving a trace to demonstrate proof of seal. Present lids for sealing medical products usually have the adhesive on the exterior portion of the lid that faces the container, usually a tray or bowl, that the lid is sealed to. Thus the adhesive is susceptible to contact with the product or device in the container. In addition, many present lids have the adhesive only at those portions that will register with a flange on the container, thus requiring a careful positioning of the lid on the container.

Also, for dry heat sterilization, a package is needed that can withstand temperatures in excess of 135° C. Currently used materials, such a polyolefins as represented by Tyvek, deform and shrink under these temperature conditions.

SUMMARY OF THE INVENTION

Thus, this invention provides a biocompatible packaging material which can withstand high temperatures of dry heat or steam heat sterilization cycles, has sufficient airflow through the material to relieve pressure in the package during sterilization, provides a barrier to penetration by bacteria, is sealable to itself or a container such as plastic trays, films, or foils, is easily opened when ready for use, and provides indication of the integrity of the seal.

Specifically, the packaging material of the invention is an air and steam-permeable, heat-resistant, bacteria-impermeable biocompatible flexible laminated composite sheet of:

a) a heat resistant polymeric nonwoven sheet bonded to b) a microporous membrane layer that is bacteria-impermeable, c) a grid patterned adhesive on the surface of the membrane layer that is opposite the sheet, which adhesive i) flows under sealing conditions to form a continuous bead around the perimeter of the sheet, ii) is substantially non-flowable or degradable when held at 140° C. for 7 hours, and iii) adheres the microporous membrane to, d) a thin, porous, heat-stable nonwoven that has open passageways, said layers selected such that the laminate has an air-permeability of between 5–150 Gurley seconds, said laminate, when sealed to a container or to itself, having a peel strength of between 1 to 5 pounds per linear inch, and exhibiting cohesive failure of the adhesive when peeled from an adherend.

The packaging material is used to form a lid, pouch or vent filter for a sterilizable package.

By "heat resistant" or "heat-stable" is meant that the laminate layers and the adhesive referred to do not substantially melt, deform, or degrade when held at 140° C. for 7 hours.

By "flows under sealing conditions" is meant that the adhesive flows upon application of a combination of heat and external pressure.

BRIEF DESCRIPTION OF THE DRAWINGS

FIG. 5a is a view of a pouch and FIG. 5b is a view taken along line a of FIG. 5a.

FIG. 8 depicts a 2-layer laminating process used in the invention.

DESCRIPTION OF THE INVENTION

The present invention comprises a non-rigid, i.e., flexible, air-permeable, bacteria-impermeable laminate for use in packaging, for example, medical devices. This laminate, as well as package components made from this laminate, is capable of withstanding dry heat sterilization at temperatures in excess of 135° C. for extended periods without adverse effects; and can be subjected to repeated dry heat sterilization cycles without damage that would jeopardize the integrity of the package or the sterility of the contents. This laminate can also be useful for other sterilization techniques such as steam or possibly ethylene oxide treatment.

An important element of the laminate is an air-permeable, bacteria-impermeable microporous membrane. By "microporous" is meant that the membrane has very small pores, i. e. micropores, that are continuous from one side of the membrane to the other. In this invention, the pores allow air flow through the membrane. For example, the airflow can range from a Frazier number of about 7 to a Gurley number of about 100. On the other hand, the pores are too small to allow passage of bacteria or pathogens through the membrane.

While a preferred microporous membrane is a hydrophobic fluoropolymer membrane such as microporous polytetrafluoroethylene; other porous polymers can be used, such as polyvinylfluoride, polyvinylidenefluoride, polychlorotrifluoroethylene, polyfluoroethylenepropylene, perfluoroalkoxyethylene and tetrafluoroethylene (TFE) copolymers, chlorotrifluoroethylene and ethylene copolymers, and TFE and ethylene copolymers. Preferably, the membrane will be from about 0.5 mils to 5 mils thick which is 12.7 to 127 micrometers thick. Preferably also the membrane will be porous expanded polytetrafluoroethylene which has an internal interconnecting porous structure made of nodes interconnected with fibrils as described in U.S. Pat. No. 3,953,566. Preferably also the void content will be 50–95% by volume. The process for its manufacture is taught in U.S. Pat. Nos. 3,953,566; 3,962,153 and 4,187,390. PTFE is heat resistant and can withstand temperatures of up to 260° C. (500° F.) or more. It is inert and non-shedding. Porous expanded PTFE can be made in a range of pore sizes. But pore size is not critical except insofar as the membrane must be air and steam permeable and bacteria impermeable. Larger pore sizes can be used with thicker membranes, the thicker membrane presenting a more tortuous path to the passage of bacteria, enabling larger pore size to function effectively as a bacterial barrier. Very small pore sizes are usable when rates of pressure change inside the package can be kept low enough to prevent damage to the laminate-to-package bond. It is preferable to select pore size to ensure good air flow as air inside the package expands as the package is heated to sterilization temperatures.

Figure 1:
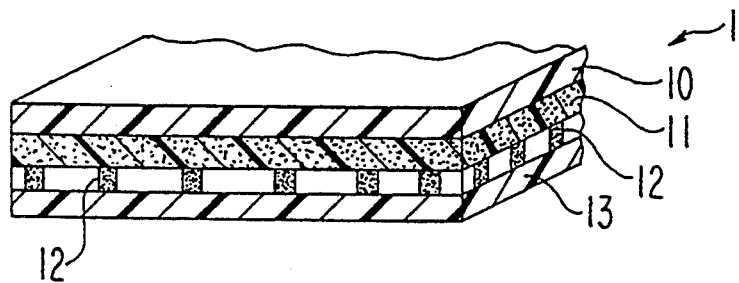
FIG. 1 is a perspective view of part of the packaging material of this invention which forms the lid of the lid/tray combination of the invention before it has been sealed onto a tray.

The microporous membrane is bonded to two heat-resistant plastic nonwoven sheets, preferably made of polymeric fibrous materials such as polypropylene or polyester. Reemay ® or Veratec ® polyester are examples. The chosen nonwoven material must be capable of withstanding the anticipated sterilization process without suffering thermal damage. Referring to FIG. 1, nonwoven 10 is preferably stiff or thick to provide support to the laminate. Nonwoven 13 is preferably less thick and has an open void structure as described below. Because the material has a lower melting point than the membrane when the membrane is PTFE, the material is easily bonded using heat and pressure directly to the surface of the membrane or can be bonded with an adhesive.

A preferred laminate 1 of this invention is prepared as follows (referring again to FIG. 1):

First, microporous membrane 11 is melt bonded to heat-resistant, plastic non-woven sheet 10 by application of heat and pressure. Next, adhesive 12 is laid down on membrane 11 in a grid pattern configured to ensure that when sealed no pathway for bacteria exists. Then, the next layer 13 of heat-resistant, plastic non-woven sheet is applied against the adhesive 12 and adhered by heat.

Thus, the adhesive is located internally in the laminate. When the laminate is used as a lid, it is placed on a tray or a bowl and sealed to the tray or bowl. Heat and pressure are applied along the seal area, and the adhesive along that area flows through the pores of nonwoven sheet 13, contacts the flange area of the tray or bowl and forms a seal. Because the adhesive is chosen so it will flow through the nonwoven sheet under sealing conditions of both heat and pressure, the adhesive flows only along the seal area and does not flow in areas where only heat and not pressure is applied.

The nonwoven sheet 13 preferably has a substantial void structure; i.e. open passageways in the structure, to facilitate flow of adhesive through it in the seal area. The fibers of the nonwoven are preferably of small diameter to aid in being encapsulated by the adhesive.

Thus the adhesive must have a number of criteria. It must provide a continuous bond between the membrane 11 and the adherend, i.e., the tray or bowl, and around the perimeter, once sealed. It must be heat stable so as to withstand steam and dry heat sterilization temperatures. It must however, be flowable under sealing conditions so as to flow through sheet 13 and seal; but, at the same time must not be flowable at the sealing temperature in areas where pressure is not applied so that it does not flow through sheet 13 in non-seal areas and drip onto the medical device inside the tray or cut off air flow. It must be bacteria-resistant. It must exhibit a cohesive failure when the lid is peeled off, so that an adhesive trace is left on the tray. This feature enables a medical attendant to readily determine the effectiveness of the original seal.

A preferred class of adhesives that meets the foregoing requirements is copolyesters. One preferred species of copolyester is polyethylene terephthalate/isophthalete resin, conveniently applied from a melt to the membrane by gravure roll printing. In one preferred embodiment, the adhesive is a blend of two different molecular weight copolyesters.

Figure 2:
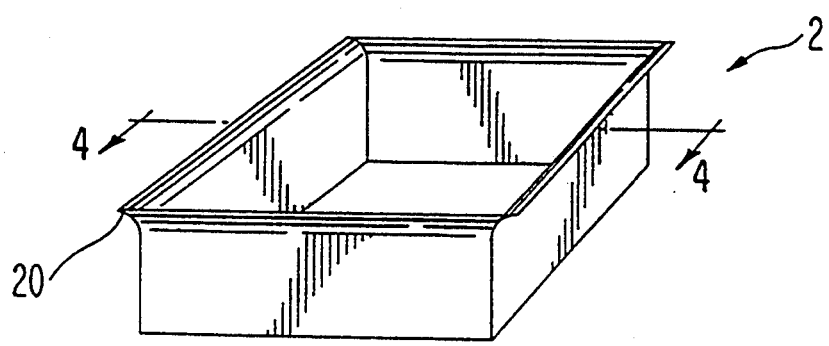
FIG. 2 is a perspective view of a tray used in this invention.
Figure 3:
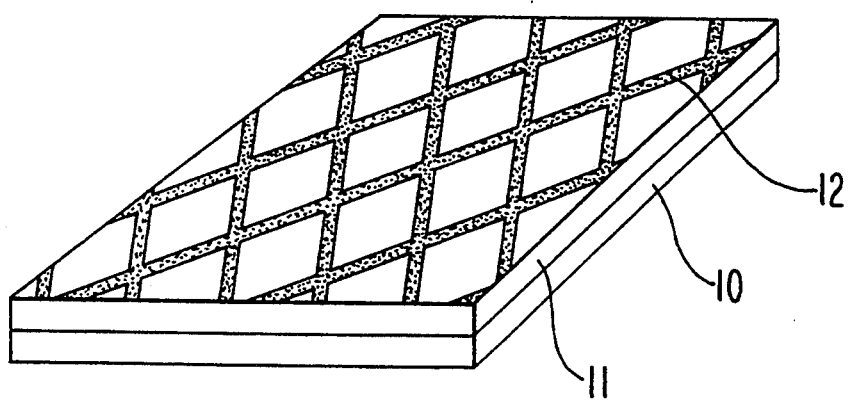
FIG. 3 depicts a portion of the lid showing location of the grid adhesive.

The laminate can be used as a lid to cover a rigid receptacle which holds a medical device. The receptacle can be made of a material that can withstand sealing and sterilization temperature and times. The receptacle, commonly referred to as a tray, is ordinarily shaped in a rigid structure by thermoforming. For convenience in sealing a lid to it, tray 2, shown in FIG. 2 ordinarily will have a flat flange 20 around the top edges to provide a surface area for contact with the lid. As FIG. 3, shows, the adhesive grid is positioned to form a continuous seal of the tray with the flange.

Figure 6A:
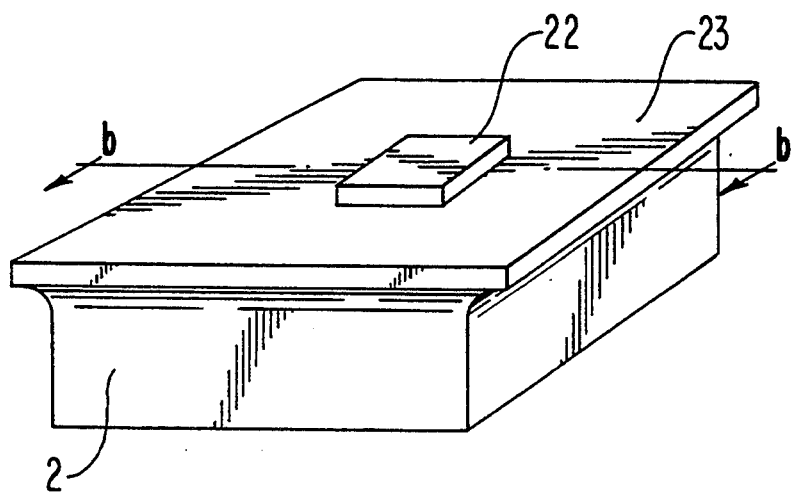
FIG. 6a and b are views of a lid and tray where the packaging material of the invention is used as a filter vent.
Figure 6B:
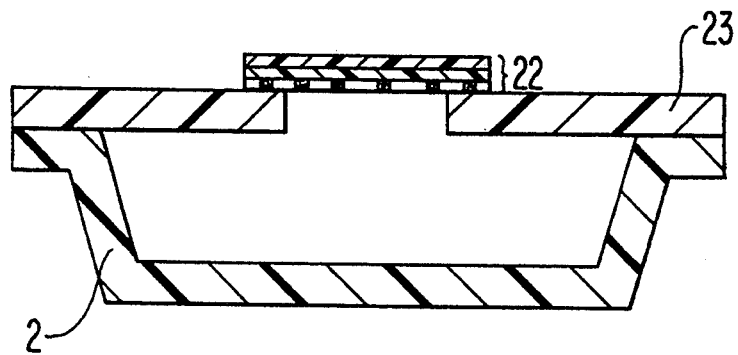

Conveniently, the entire lid for the tray is made of the material of this invention; although, if desired, the lid can be made of a plastic, or foil, like that used for the tray, with one or more openings cut in the lid that are sealed with the material of the invention, as is shown in FIGS. 6a and 6b.

Figure 4:
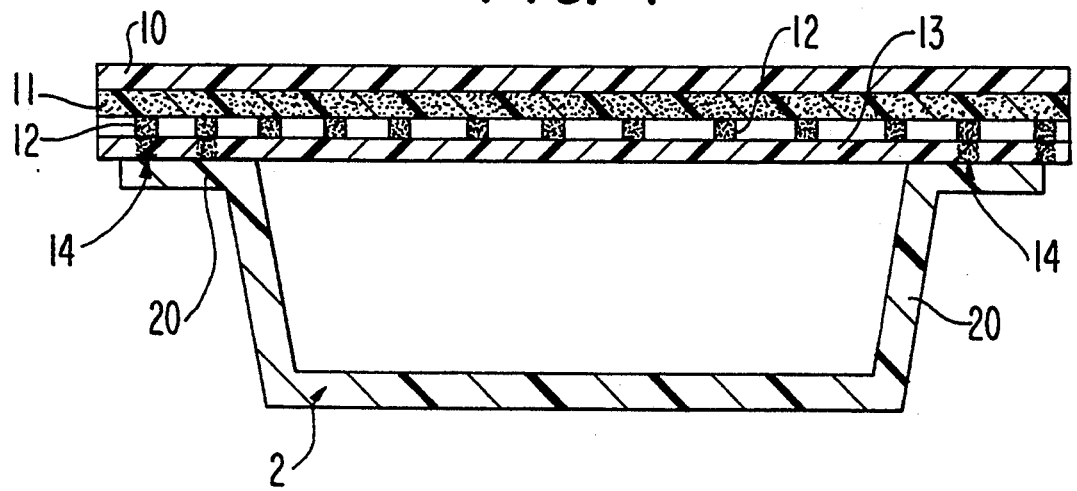
FIG. 4 is a cut-away side view of the lid and tray of the invention where the lid and tray have been sealed. The view is taken along 4—4 of FIG. 2.

After the device or material to be packaged has been placed into the tray, he lid made of the laminate of this invention is placed onto the tray with nonwoven 13 closet to the tray flange. Heat and pressure are applied for a suitable period of time. Adhesion is obtained by softening of the adhesive, causing it to flow through the nonwoven 13, as shown in FIG. 4., and contacting the tray 20, where the lid bonds to the tray at 14. The pattern of adhesive 13 flows through nonwoven 13 to contact and adhere lid 1 to tray 2 at contact point 14. The tray is preferably made of a rigid heat tolerant plastic such as heat resistant polycarbonate, polysulfone, polyphthalate carbonates, polypropylene and the like.

The seal must be capable of withstanding exposure to the heat and pressure cycles of sterilization while maintaining integrity of the seal. Likewise, the sealing strength after sterilization must not be so high as to require excessive force when the lid is peeled from the tray during opening of the package. The amount of adhesion or bonding (the amount of force required to peel the adhered lid from the tray) is typically known as peel strength; measurement techniques for determining peel strength are well known to those skilled in the art. Furthermore, to present evidence of an effective seal, the adhesive should be one that leaves an adhesive trace on the flange after the lid is peeled away.

This package can be doubled if desired, that is the first sealed package can be sealed within a second lid and tray of similar design but larger dimensions. When this double package is sealed and sterilized, it allows the exterior of the inner package to remain sterile while the outer package is exposed to a non-sterile environment. Double packages are well known to those skilled in the art of medical device packaging and are of particular value in the packaging and subsequent sterilization of manufactured medical devices.

Figure 5A:
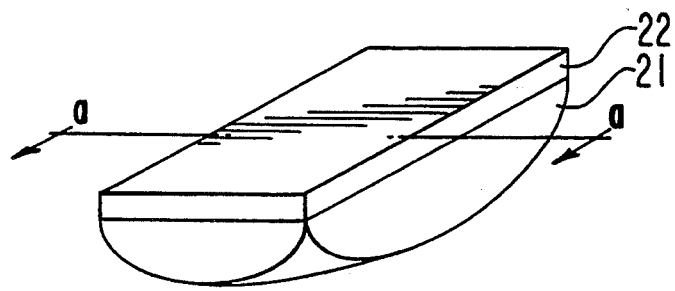
Figure 5B:
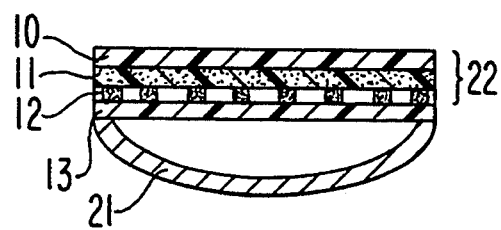

To form a pouch as shown in FIG. 5a and b, the flexible material 21 can be plastic film or a metal foil, or a metal foil that is coated with plastic, such as polypropylene, polyester or polycarbonate. To form the pouch, the medical device is placed between laminate 22 and material 21 and the edges of the two halves sealed by heat and pressure to fuse them, much as the sealing occurs as described about with respect to the lid and tray.

The laminate can also be used a filter vent as shown in FIGS. 6a and 6b where the laminate is 22 and covers a vent or hole in packaging top 23.

Test Procedures

Bubble Point

The pore size of the expanded porous polytetrafluoroethylene membranes can be determined relatively by determining the bubble point of the membranes. The bubble point is the pressure of air required to blow the first continuous bubbles detectable by their rise through a layer of isopropyl alcohol covering the PTFE media. The bubble point of porous PTFE was measured using isopropyl alcohol following ASTM F316-86. In general, the bubble point of the membranes useful in this invention ranges from 1 psi to 30 psi.

Gurley Number

Gurley Number provides an indication of the degree of air flow through a membrane. A Gurley densometer manufactured by W. & L.E. Gurley & Sons (ASTM D726-58) was used. Gurley number is determined by the time it takes for 100 cc air to flow through 1 inch square orifice, at a pressure drop of 4.88 inches of water.

Frazier Number

Air permeability was measured by clamping a test sample in a gasketed flanged fixture which provided in circular area of approximately 6 square inches (2.75 inches diameter) for air flow measurement. The upstream side of the sample fixture was connected to a flow meter in line with a source of dry compressed air. The downstream side of the sample fixture was open to the atmosphere.

Testing was accomplished by applying a pressure of 0.5 inches of water to the upstream side of the sample and recording the flow rate of the air passing through the in-line flowmeter (a ball-float rotameter).

The sample was conditioned at 70° F. and 65% relative humidity for at least 4 hours prior to testing.

Results are reported in terms of Frazier Number which is air flow in cubic feet/minute/square foot of sample at 0.5 inches water pressure.

Peel Strength

Peel strength testing gives a measure of not only the integrity of the package, but also the ease of opening. 180° peel testing was performed according to ASTM D903-49 under the conditions as follows. Four, 1 inch (2.54 cm) strips were cut from each sealed bowl (see Example 2), at 90° intervals, perpendicular to, and through, the flange of each sealed bowl to obtain samples of the sealed region of the flange of the bowl. A Vinatoru model RFD 1048 peel apparatus was employed with the flexible member (lid) placed in the actuated grip and the stiff member (bowl) placed in the fixed grip. The actuated grip traveled at a rate of 200 mm/min. Raw data was collected in kg/linear inch over the length of the peel (flange width).

EXAMPLE I

This example demonstrates the preparation of one embodiment of a packaging material laminate of the invention.

The following materials were employed, with reference to the numerals on the figures:

a polyester nonwoven sheet 10 having 1.5 and 3 denier fibers and a basis weight of 2.6 oz./yd$^2$ (88.2 gm/m$^2$) obtained from Veratec Corp. as part no. SM 519, 5 mil (127 microns) thick;

a microporous expanded polytetrafluoroethylene membrane 11 (ePTFE) obtained from W. L. Gore & Associates, Inc. having a nominal pore size of 0.1 micron, a bubble point of about 25 psi (1.76 kg/cm$^2$) and an air flow of 3 Gurley seconds, 0.5 mil (12.7 microns) thick;

a preshrunk polyester nonwoven 13 having a fiber size of 1.5 and 3.0 denier and a weight of 1.0 oz/yd$^2$ (33.9 gm/m$^2$) (Veratec Corp. SR 524), 1 mil (25.4 microns) thick;

a polyester adhesive 12 made by employing polyethylene terephthalate/isophthalate copolyester (obtained as Vitel #1050 from Goodyear Tire and Rubber) and blending at a ratio of 9:1 with a polyethylene terephthalate based branched, low molecular weight copolyester (obtained as Vitel 5833 from Goodyear). Blending was carried out in a Werner and Pfleiderer twin screw extruder.

The first step of laminate preparation was bonding the polyester nonwoven 10 to the microporous ePTFE membrane 11. These two materials were laminated by a combination of heat and pressure, using a heated chrome roll 30 and two silicone nip rolls 31 and 33, as shown in FIG. 8. Temperatures used were in excess of 240° C., to allow softening of the nonwoven polyester. Once the nonwoven polyester had softened, the nip rolls were used to apply pressure to the two materials, thereby fusing both layers together.

Figure 7:
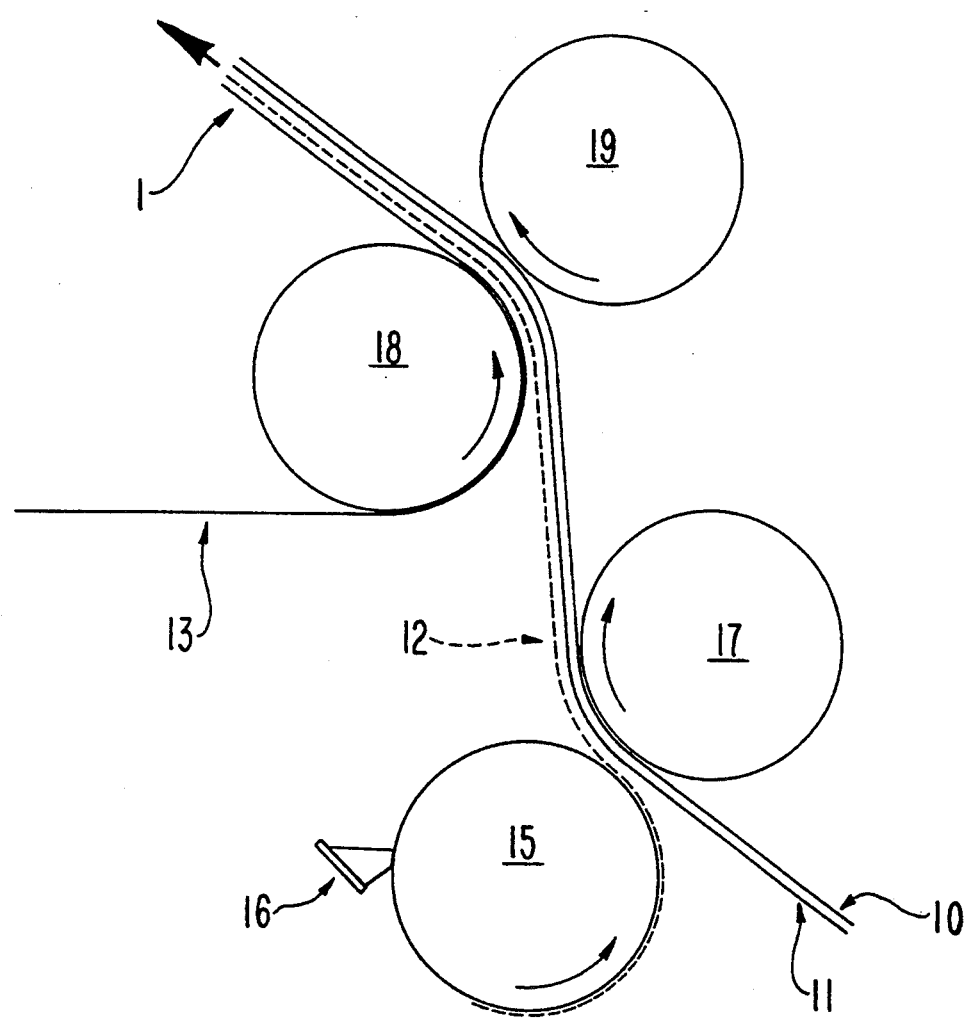
FIG. 7 is a diagram of the process sequence for preparing the packaging material of the invention.

Next, and in reference to FIG. 7, a gravure printer/laminator combination was used that produced a 0.42 m wide laminate.

The gravure printer comprised a grid pattern engraved roll 15 that had sixteen lines per linear inch, each with a depth of 300 microns. It was nipped at 519.15 kPa to a silicone rubber roll 17 of 65 shore A durometer hardness.

The laminator portion comprised a chrome roll 18 roll nipped at 346.1 kPa to a silicon rubber roll 19 of 65 shore A durometer hardness. Gravure roll 15 was heated to 250°-255° C. The silicone roll was nipped to gravure roll 15 was at 125° C. Chrome roll 18 was also heated to 125° C. while the rubber roll 19 nipped to chrome roll 18 was at ambient temperature. Gravure roll 15 was in contact with trough 16 containing polyester adhesive 12 in a molten state. Trough 16 was maintained at 235°–250° C. under a nitrogen blanket to prevent degradation of the polyester adhesive. The polyester adhesive was transferred from gravure roll 15 onto the microporous membrane side 11 of the two layer laminate in a controlled amount so as to form a grid pattern on the membrane when it contacted roll 17. The microporous membrane/nonwoven into which the polyester adhesive had been partially forced was combined with polyester nonwoven 13 and adhered by passage between the nips of rolls 18 and 19. The line ran at a rate of 8 ft./min. (2.44 m/min.) to produce the laminated sheet.

Biocompatability

Biocompatability of the laminated sheet of Example 1 was tested by subjecting the sheet to USP Biological Tests Classification VI, with the following results:

Acute Systemic Toxicity (USP): The saline, alcohol in saline, polyethylene glycol 400 and cottonseed oil extracts of the test article injected into mice did not produce a significantly greater systemic reaction than the blank extractant.

Intracutaneous Toxicity (USP): The saline, alcohol in saline, polyethylene glycol 400 and cottonseed oil extracts of the test article injected intracutaneously in rabbits did not produce a significantly greater tissue reaction than the blank extractant.

Implantation Test (USP): The macroscopic reaction of the test article implanted 7 days was not significant as compared to the USP negative control plastic.

The sample of test article extracted at a ratio of 120 sq. cm/20 ml and at a temperature of 121° C. for 1 hour met the requirements of a USP Class VI Plastic.

EXAMPLE 2

Preparation and Sealing of Lid to Tray

The laminated sheet was sealed to a tray in the shape of a flanged bowl. The bowls outer diameter was 6.59 inches (167.48 mm); the flange on the bowl was 0.45 inches (11.43 mm); and the laminated sheet (which formed the lid) was about the same diameter as the bowl. Sealing was carried out by the use of a standard package sealing machine. In this example a Belco Engineering Model BM2020 heated platen sealing machine with controllable pressure, temperature, and dwell time was used. This machine has an 8 inch (20.32 cm) air cylinder, a 0–30 second dwell timer, and a microprocessor controlled temperature controller. A thermoformed bowl made of high temperature polycarbonate (APEC HT DP9-9350 from Miles, Inc.) was placed on a supported silicone ring on the machine. A flat lid of the same dimension of the bowl was cut from the laminated sheet and placed on top of the bowl and oriented such that the adhesive bonded nonwoven side faced the flange of the thermoform. The unsealed lid and bowl were placed into the seal area of the machine and sealed at a given range of sealing parameters. In this example, sealing temperatures in the range of 125°–135° C. were used, with dwell times of 25–30 seconds and pressures in the range of 70–80 psi. These parameters produced sealed packages with a desired degree of peel characteristics when opened.

EXAMPLE 3

Dry Heat Sterilization of Packages

A package, sealed as in Example 2, was placed into a dry heat sterilizer. The sterilizer was fully programmable with respect to set points, ramp rates, and cooling rates. The sterilizer was set to a temperature of 140° C., and the total time was set to 7–8 hours. Sterilization time will be dependent on the type of package and the device. After complete sterilization, the package was removed. The package seals remained integral. The packages could be opened by hand, and evidence of adhesive was left on the flange.

Six lids were sealed to bowls under the conditions of temperature 260°–275° F., pressure 80 psi, and time 30 sec. These samples were then sterilized under conditions (as described above). Resulting peel strengths were in the range of 1.3–3.4 pounds/linear inch.

Twelve sealed and sterilized packages (prepared as in the Examples) were used in a bacterial challenge test (10 samples and one positive control, and one negative control). The 10 samples and the positive control were placed in a bacterial challenge chamber. The negative control does not undergo the challenge. Spores of *Bacillus subtilis* ATCC 9372 were used as the challenge organism. A total of 0.2 ml of $1 \times 10^6$/ml *Bacillus subtilis* spore preparation were used as the inoculum. After the challenge, the packages were exposed in a UV chamber for one minute and the contents of the packages were sterility tested. Sterility testing consisted of aseptically pouring 300 mls of sterile molten Trypticase Soy Agar (TSA) into the packages. Testing in this manner detects a breach in the package integrity.

The results were as follows:

The Positive control remained positive (i.e., no breach) after 3 days incubation. The Negative control remained negative after 3 days incubation. The Tested Packages:

| Number of Units Exposed | Number Demonstrating Growth |
|---|---|
| 11 (10 samples + pos. cont.) | 0 |

Thus, the packages provided an efficient barrier to maintain the sterility of the contents of the package.

We claim:

1. A packaging material that is and steam-permeable, heat-resistant, and bacteria-impermeable, which comprises a biocompatible flexible laminated composite sheet having the following layers:
   a) a heat resistant polymeric nonwoven sheet bonded to
   b) a microporous membrane layer that is bacteria-impermeable,
   c) a grid patterned adhesive on the surface of the membrane layer that is opposite the sheet, which adhesive
      i) flows under sealing conditions to form a continuous seal around the perimeter of the sheet, and,
      ii) is substantially non-flowable or degradable when held at 140° C. for 7 hours, and
      iii) adheres the microporous membrane, to,
   d) a thin, porous, heat-stable nonwoven, that has open passageways, said layers selected such that the laminate has an air-permeability of between 5 and 150 Gurley seconds, said laminate, when sealed to a container or itself, having a peel strength of between 1 to 5 pounds per linear inch, and exhibiting cohesive failure of the adhesive when peeled from an adherend.

2. The laminate of claim 1 in the form of a pouch.

3. The laminate of claim 1 in the form of a packaging lid.

4. The laminate of claim 1 wherein the adhesive is a blend of two different molecular weight polyethylene terephthalate/isophthalate copolyesters.

* * * * *